(12) United States Patent
Lee (10) Patent No.: US 12,022,880 B2
(45) Date of Patent: Jul. 2, 2024

(54) AEROSOL GENERATING DEVICE PREVENTING REUSE OF AN AEROSOL GENERATING ARTICLE BY DETECTING DISCOLORATION OF A WRAPPER OF THE AEROSOL GENERATING ARTICLE

(71) Applicant: KT&G CORPORATION, Daejeon (KR)

(72) Inventor: Moon Bong Lee, Seoul (KR)

(73) Assignee: KT&G CORPORATION, Daejeon (KR)

( * ) Notice: Subject to any disclaimer, the term of this patent is extended or adjusted under 35 U.S.C. 154(b) by 602 days.

(21) Appl. No.: 17/275,875

(22) PCT Filed: Dec. 11, 2020

(86) PCT No.: PCT/KR2020/018171
§ 371 (c)(1),
(2) Date: Mar. 12, 2021

(87) PCT Pub. No.: WO2021/141259
PCT Pub. Date: Jul. 15, 2021

(65) Prior Publication Data
US 2022/0400767 A1 Dec. 22, 2022

(30) Foreign Application Priority Data

Jan. 6, 2020 (KR) .......... 10-2020-0001706
Apr. 6, 2020 (KR) .......... 10-2020-0041538

(51) Int. Cl.
*A24F 40/51* (2020.01)
*A24D 1/02* (2006.01)
(Continued)

(52) U.S. Cl.
CPC ............... *A24F 40/51* (2020.01); *A24D 1/02* (2013.01); *A24D 1/20* (2020.01); *A24F 40/20* (2020.01); *A24F 40/60* (2020.01); *G01N 21/31* (2013.01)

(58) Field of Classification Search
CPC ............ A24F 40/51; A24F 40/20; A24D 1/02
See application file for complete search history.

(56) References Cited

U.S. PATENT DOCUMENTS

| 4,947,874 A | 8/1990 | Brooks et al. |
| 5,526,559 A | 6/1996 | Fleenor et al. |

(Continued)

FOREIGN PATENT DOCUMENTS

| CA | 3 099 825 A1 | 11/2019 |
| CN | 1045691 A | 10/1990 |

(Continued)

OTHER PUBLICATIONS

Office Action dated Dec. 15, 2021 in Korean Application No. 10-2020-0028582.
(Continued)

*Primary Examiner* — Hae Moon Hyeon
(74) *Attorney, Agent, or Firm* — Sughrue Mion, PLLC (57) ABSTRACT

Provided is an aerosol generating system including an aerosol generating article and an aerosol generating device configured to receive and heat the aerosol generating article. The aerosol generating article includes a wrapper that is heated to be discolored, and the aerosol generating device includes a sensor that is configured to detect a discoloration of the wrapper.

12 Claims, 4 Drawing Sheets

(51) Int. Cl.
  *A24D 1/20* (2020.01)
  *A24F 40/20* (2020.01)
  *A24F 40/60* (2020.01)
  *G01N 21/31* (2006.01)

(56) References Cited

U.S. PATENT DOCUMENTS

| | | | |
|---|---|---|---|
| 8,689,804 B2* | 4/2014 | Fernando | H05B 1/0244 |
| | | | 131/184.1 |
| 9,814,265 B2 | 11/2017 | Rinker et al. | |
| 10,729,178 B2 | 8/2020 | Reevell | |
| 10,869,499 B2 | 12/2020 | Fernando et al. | |
| 10,918,136 B2 | 2/2021 | Reevell | |
| 10,993,473 B2 | 5/2021 | Malgat et al. | |
| 11,330,835 B2 | 5/2022 | Lavanchy | |
| 2011/0192408 A1 | 8/2011 | Inagaki et al. | |
| 2015/0013696 A1 | 1/2015 | Plojoux et al. | |
| 2016/0302488 A1 | 10/2016 | Fernando et al. | |
| 2017/0055581 A1 | 3/2017 | Wilke et al. | |
| 2017/0071251 A1 | 3/2017 | Goch | |
| 2017/0143039 A1 | 5/2017 | Buehler et al. | |
| 2017/0191020 A1 | 7/2017 | Recht et al. | |
| 2017/0196268 A1 | 7/2017 | Reevell | |
| 2017/0231277 A1 | 8/2017 | Mironov et al. | |
| 2017/0340008 A1* | 11/2017 | Sebastian | A24D 1/025 |
| 2018/0220713 A1 | 8/2018 | Chang et al. | |
| 2018/0228213 A1 | 8/2018 | Buehler et al. | |
| 2018/0242638 A1 | 8/2018 | Godfrey et al. | |
| 2019/0000141 A1 | 1/2019 | Rojo-Calderon et al. | |
| 2019/0014820 A1 | 1/2019 | Malgat | |
| 2019/0045844 A1 | 2/2019 | Reevell | |
| 2019/0230989 A1 | 8/2019 | Fursa et al. | |
| 2019/0261684 A1 | 8/2019 | Reevell | |
| 2020/0093185 A1 | 3/2020 | Lim | |
| 2020/0154765 A1 | 5/2020 | Lee et al. | |
| 2020/0196665 A1 | 6/2020 | Bilat et al. | |
| 2020/0232766 A1 | 7/2020 | Flick | |
| 2020/0260790 A1 | 8/2020 | Kaufman et al. | |
| 2020/0281254 A1* | 9/2020 | Rogan | C09D 11/037 |
| 2020/0305508 A1 | 10/2020 | Talon | |
| 2020/0316325 A1 | 10/2020 | Reevell | |
| 2021/0007400 A1 | 1/2021 | Liu et al. | |
| 2021/0237214 A1 | 8/2021 | Guenther et al. | |
| 2023/0240353 A1* | 8/2023 | Kulkarni | A24F 40/50 |
| | | | 131/328 |

FOREIGN PATENT DOCUMENTS

| | | |
|---|---|---|
| CN | 106455726 A | 2/2017 |
| CN | 106292402 A | 7/2017 |
| CN | 107713009 A | 2/2018 |
| CN | 107775187 A | 3/2018 |
| CN | 107846978 A | 3/2018 |
| CN | 107949287 A | 4/2018 |
| CN | 108366618 A | 8/2018 |
| CN | 108601396 A | 9/2018 |
| CN | 109363243 A | 2/2019 |
| CN | 109640717 A | 4/2019 |
| CN | 209498553 U | 10/2019 |
| DE | 20 2014 001 718 U1 | 7/2015 |
| EP | 2 468 118 A1 | 6/2012 |
| EP | 3 175 721 A1 | 6/2017 |
| EP | 3 574 774 A1 | 12/2019 |
| EP | 3 718 419 A1 | 10/2020 |
| EP | 3 831 223 A1 | 6/2021 |
| GB | 2 259 135 A | 3/1993 |
| JP | 9-222361 A | 8/1997 |
| JP | 11-6767 A | 1/1999 |
| JP | 11-178561 A | 7/1999 |
| JP | 2018-527918 A | 9/2018 |
| JP | 2019-506855 A | 3/2019 |
| KR | 10-0889660 B1 | 3/2009 |
| KR | 10-2011-0096548 A | 8/2011 |
| KR | 10-2013-0001750 A | 1/2013 |
| KR | 10-2014-0067691 A | 6/2014 |
| KR | 10-2014-0084769 A | 7/2014 |
| KR | 10-2014-0121381 A | 10/2014 |
| KR | 10-2015-0144089 A | 12/2015 |
| KR | 10-2016-0096585 A | 8/2016 |
| KR | 10-1776966 B1 | 9/2017 |
| KR | 10-2018-0056643 A | 5/2018 |
| KR | 10-2018-0099674 A | 9/2018 |
| KR | 10-2018-0100319 A | 9/2018 |
| KR | 10-2018-0120166 A | 11/2018 |
| KR | 10-2018-0129637 A | 12/2018 |
| KR | 10-2019-0011721 A | 2/2019 |
| KR | 10-2019-0012150 A | 2/2019 |
| KR | 10-1971169 B1 | 4/2019 |
| KR | 10-2019-0051745 A | 5/2019 |
| KR | 10-2019-0129757 A | 11/2019 |
| KR | 10-2019-0134855 A | 12/2019 |
| KR | 10-2019-0143177 A | 12/2019 |
| KR | 10-2020-0000635 A | 1/2020 |
| TW | 201618682 A | 6/2016 |
| WO | 2016/026811 A1 | 2/2016 |
| WO | 2017/114895 A1 | 7/2017 |
| WO | 2017/118557 A1 | 7/2017 |
| WO | 2018/050701 A1 | 3/2018 |
| WO | 2018/190606 A1 | 10/2018 |
| WO | 2019/090200 A1 | 5/2019 |
| WO | 2019/129378 A1 | 7/2019 |
| WO | WO-2019129378 A1 * | 7/2019 ............ A24C 5/601 |
| WO | 2019/197413 A1 | 10/2019 |
| WO | 2019/224310 A1 | 11/2019 |
| WO | WO-2021122475 A1 * | 6/2021 ............ A24D 1/02 |
| WO | WO-2021249833 A1 * | 12/2021 |

OTHER PUBLICATIONS

Office Action dated Dec. 15, 2021 in Korean Application No. 10-2020-0041537.
Office Action dated Dec. 17, 2021 in Korean Application No. 10-2020-0047420.
Extended European Search Report dated Nov. 5, 2021 in European Application No. 20855894.0.
Extended European Search Report dated Oct. 15, 2021 in European Application No. 20866967.1.
Extended European Search Report dated Dec. 8, 2021 in European Application No. 20866966.3.
Office Action dated Apr. 14, 2023 from the Chinese Patent Office in Application No. 202080006484.4.
Office Action dated Apr. 15, 2023 from the Chinese Patent Office in Application No. 202080006550.8.
Office Action dated Apr. 17, 2023 from the Chinese Patent Office in Application No. 202080006491.4.
Office Action dated Jun. 21, 2022 issued by the Korean Patent Office in Korean Application No. 10-2020- 0041538.
Office Action dated Jul. 19, 2022 issued by the Japanese Patent Office in Japanese Application No. 2021-534382.
Office Action dated Jul. 12, 2022 issued by the Japanese Patent Office in Japanese Application No. 2021-529309.
International Search Report dated Mar. 16, 2021 from the International Searching Authority in International Application No. PCT/KR2020/018035.
International Search Report dated Mar. 16, 2021 from the International Searching Authority in International Application No. PCT/KR2020/017923.
International Search Report dated Mar. 17, 2021 from the International Searching Authority in International Application No. PCT/KR2020/018171.
Tong Ying, "Research on the Key Technologies of Stereo Vision Based on Infrared and Visible Dual Band Images", China Doctoral Dissertation Full Text Database Information Technology Series, Tianjin University, 2015 (122 pages total).
Office Action dated Sep. 26, 2023 in Chinese Application No. 202080006491.4.

(56) References Cited

OTHER PUBLICATIONS

European Office Action dated Mar. 13, 2024 in Application No. 20 866 967.1.

* cited by examiner

AEROSOL GENERATING DEVICE PREVENTING REUSE OF AN AEROSOL GENERATING ARTICLE BY DETECTING DISCOLORATION OF A WRAPPER OF THE AEROSOL GENERATING ARTICLE

TECHNICAL FIELD

The disclosure relates to an aerosol generating system, and more particularly, to an aerosol generating system including an aerosol generating article and an aerosol generating device that detects discoloration of a wrapper of the aerosol generating article.

BACKGROUND ART

Recently, the demand for alternative methods to overcome the disadvantages of traditional cigarettes has increased. For example, there is growing demand for an aerosol generating device which generates aerosol by heating an aerosol generating material in cigarettes, rather than by combusting cigarettes. Accordingly, research on a heating-type aerosol generating device have been actively conducted.

Technical Problem

The aerosol generating device users may insert aerosol generating articles into aerosol generating devices to use the aerosol generating devices. In general, an aerosol generating article that is disposable is first inserted into an aerosol generating device and then discarded after the use.

However, instead of discarding the aerosol generating article that is first inserted and used, some users may reuse the aerosol generating article. The reuse of the aerosol generating article may change a component for generating a flavor of an aerosol in the aerosol generating article, and thus, the user may feel unpleasant.

Therefore, there is a need to prevent a change in the flavor of the aerosol by averting the reuse of the aerosol generating article, and configurations and methods for such prevention need to be applied to aerosol generating articles and/or aerosol generating devices.

One or more embodiments provide an aerosol generating device that prevents reuse of an aerosol generating article by detecting discoloration of a wrapper of the aerosol generating article.

One or more embodiments provide an aerosol generating system that includes an aerosol generating article and an aerosol generating device that prevents reuse of the aerosol generating article.

The technical problems of the present disclosure are not limited to the aforementioned description, and other technical problems may be solved from the embodiments described hereinafter.

Technical Solution

According to one or more embodiments, there is provided an aerosol generating system including an aerosol generating article and an aerosol generating device that accommodates and heats the aerosol generating article, wherein the aerosol generating article includes a wrapper that is heated and discolored by the aerosol generating device, and the aerosol generating device includes a sensor that detects discoloration of the wrapper.

Advantageous Effects

An aerosol generating article includes a wrapper that is discolored when the aerosol generating article is heated and used. An aerosol generating system according to embodiments may detect re-insertion and/or reuse of the aerosol generating article by detecting the discoloration of the wrapper of the inserted aerosol generating article.

The aerosol generating device may include a sensor that is mounted on an accommodation unit, into which the aerosol generating article is inserted, and detects the discoloration of the wrapper. When the discoloration of the wrapper is detected by the sensor, the aerosol generating device may determine that the reuse of the aerosol generating article has occurred.

When the reuse of the aerosol generating article is detected, the operation of the aerosol generating device may be blocked. Alternatively, the reuse of the aerosol generating article may be notified to the user by an alarm unit installed in the aerosol generating device.

As the reuse of the aerosol generating article is prevented, a decrease in satisfaction due to a change in an aerosol flavor may be mitigated.

BEST MODE

According to one or more embodiments, an aerosol generating system includes an aerosol generating article and an aerosol generating device configured to receive and heat the aerosol generating article, wherein the aerosol generating article includes a wrapper that is heated and discolored by the aerosol generating device, and the aerosol generating device includes a sensor that is configured to detect a discoloration of the wrapper.

The aerosol generating article may be inserted into an accommodation unit of the aerosol generating device, the sensor may be mounted inside the accommodation unit, and based on the aerosol generating article being inserted into the accommodation unit, the wrapper is positioned to be adjacent to the sensor.

The sensor may be mounted in a cavity formed inside the accommodation unit.

The aerosol generating article may include a tobacco rod, a front-end plug arranged on a side of the tobacco rod, and a filter rod arranged on the other side of the tobacco rod, wherein the wrapper may be wrapped around the tobacco rod, the front-end plug, and the filter rod, and the wrapper may be discolored at a temperature between about 50° C. and about 300° C.

The wrapper may include a first area at a first periphery of the front-end plug, a second area at a second periphery of the tobacco rod, and a third area at a third periphery of the filter rod, and the wrapper may be discolored in at least one of the first area, the second area, and the third area.

The wrapper may include a thermochromic material in at least one of the first area, the second area, and the third area.

The thermochromic material may include at least any one of a cellulous-based material, a starch-based material, a polyamide-based material, an organic acid, and a pigment.

The sensor may include a light source configured to emit light to the aerosol generating article; and a vision sensor configured to receive light reflected from the aerosol generating article to detect the discoloration.

The aerosol generating system may further include a controller that is electrically connected to the sensor, wherein, based on the discoloration of the wrapper being detected, the sensor may be configured to transmit a discoloration detection signal to the controller.

When the controller receives the discoloration detection signal, the controller may be configured to block operation of the aerosol generating device.

When the controller receives the discoloration detection signal, the controller may be configured to generate an alarm signal that notifies a user of the reuse of the aerosol generating article.

When the controller receives the discoloration detection signal, the controller may be configured to generate an alarm signal that notifies a user of the reuse of the aerosol generating article.

The aerosol generating system may further include an alarm unit including at least one of a vibrator, a speaker, and a display, and the alarm unit may be configured to transmit, to the user, at least one of a vibration, a sound, and a light output in response to the alarm signal from the controller.

According to one or more embodiments, an aerosol generating device includes an accommodation unit configured to receive an aerosol generating article including a wrapper, a sensor configured to detect a discoloration of the wrapper and a controller electrically connected to the sensor, wherein, based on the discoloration of the wrapper being detected, the sensor is configured to transmit a discoloration detection signal to the controller.

The sensor may include a light source configured to emit light to the aerosol generating article; and a vision sensor configured to receive light reflected from the aerosol generating article to detect the discoloration.

MODE

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

It will be understood that when an element or layer is referred to as being "over," "above," "on," "connected to" or "coupled to" another element or layer, it can be directly over, above, on, connected or coupled to the other element or layer or intervening elements or layers may be present. In contrast, when an element is referred to as being "directly over," "directly above," "directly on," "directly connected to" or "directly coupled to" another element or layer, there are no intervening elements or layers present. Like numerals refer to like elements throughout.

With respect to the terms used to describe in the various embodiments, the general terms which are currently and widely used are selected in consideration of functions of structural elements in the various embodiments of the present disclosure. However, meanings of the terms can be changed according to intention of one of ordinary skill in the art, judicial precedents, an emergence of a new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and in the context of the descriptions provided herein.

In addition, unless explicitly indicated otherwise, the word "comprise" and variations such as "comprises" or "comprising" will be understood to imply the inclusion of stated elements but not the exclusion of any other elements. In addition, the terms "-er", "-or", and "module" may mean units for processing at least one function and/or operation and can be implemented by hardware components or software components and/or combinations thereof.

Embodiments of the disclosure are arbitrarily divided to easily describe the inventive concept and need not be mutually exclusive. For example, structures described in an embodiment may be applied to other embodiments and embodied therein, and various changes in form and details can be made therein without departing from the spirit and scope of the disclosure.

The terms used in the various embodiments of the present disclosure are to describe the embodiments, but are not intended to limit the embodiments. In the present disclosure, the singular forms are intended to include the plural forms as well, unless the context specifically indicates otherwise.

Throughout the disclosure, a "lengthwise direction" of a component may be a direction in which the component extends along an axis of one direction of the component, and the axis of one axis of the component may be a direction in which the component extends longer than the other direction crossing the axis.

Hereinafter, one or more inventive concepts will now be described more fully with reference to the accompanying drawings, in which exemplary embodiments of the present disclosure are shown such that one of ordinary skill in the art may easily understand and practice the embodiments of the disclosure. The inventive concept may, however, be embodied in many different forms and should not be construed as being limited to the embodiments set forth herein.

Figure 1:
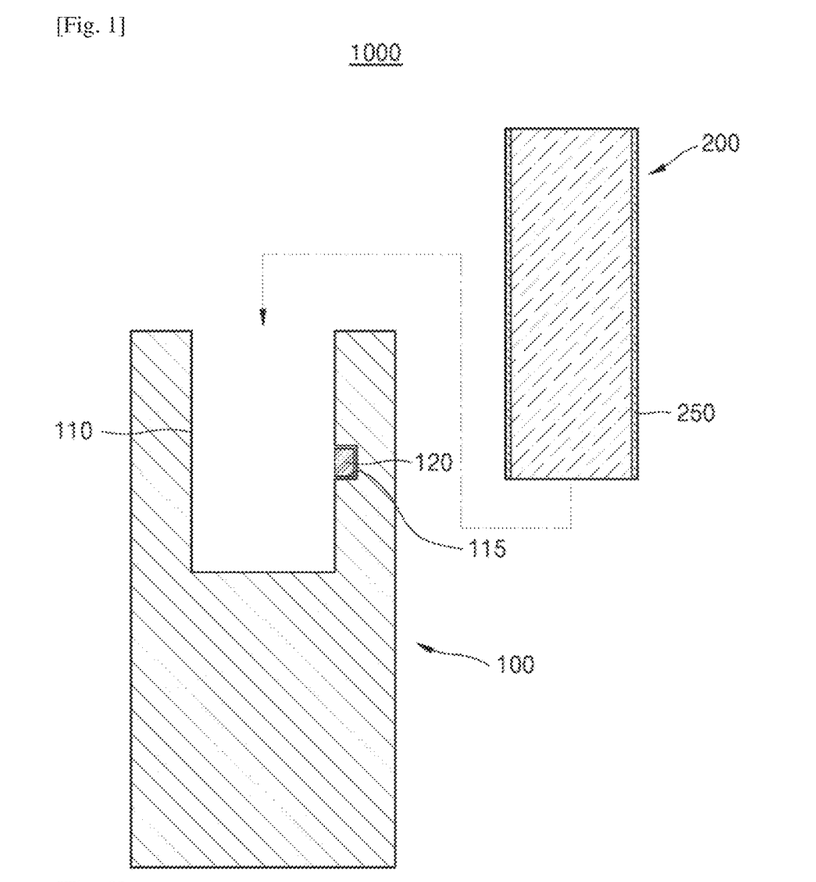
FIG. 1 is a cross-sectional view of an aerosol generating system including an aerosol generating device and an aerosol generating article, according to an embodiment.

FIG. 1 is a cross-sectional view of an aerosol generating system 1000 including an aerosol generating device 100 and an aerosol generating article 200, according to an embodiment.

The aerosol generating system 1000 according to an embodiment includes the aerosol generating article 200 and the aerosol generating device 100 that receives and heats the aerosol generating article 200.

The aerosol generating article 200 may be inserted into an accommodation unit 110 of the aerosol generating device 100. The aerosol generating article 200 may include a wrapper 250 that is heated after being inserted into the accommodation unit 110 of the aerosol generating device 100 and is discolored. In this case, the wrapper 250 may form an outer surface of the aerosol generating article 200.

Shapes of the aerosol generating article 200 and the accommodation unit 110 may correspond to each other. For example, when the aerosol generating article 200 has a cylindrical shape, the accommodation unit 110 may also have a cylindrical shape to accommodate the aerosol generating article 200. However, the shapes of the aerosol generating article 200 and the accommodation unit 110 are not limited thereto and may change according to the necessity.

The aerosol generating device 100 includes a sensor 120 that detects the discoloration of the wrapper 250. The sensor 120 may be disposed in the accommodation unit 110. For example, the sensor 120 may be disposed in a certain cavity 115 formed on an internal surface of the accommodation unit 110. When the aerosol generating article 200 is inserted into the accommodation unit 110, the sensor 120 may be adjacent to the wrapper 250 of the aerosol generating article 200.

The sensor 120 may be disposed at a location corresponding to a portion of the wrapper 250 that is discolored. That is, in a lengthwise direction of the aerosol generating article 200, a height of the discolored portion of the wrapper 250 may be identical to a height of a portion, on which the sensor 120 is disposed, with respect to a lower surface of the accommodation unit 110.

FIG. 1 illustrates components of the aerosol generating device 100 according to an embodiment. Therefore, it will be understood by one of ordinary skill in the art related to the present embodiment that other components may be further included in the aerosol generating device 100, in addition to the components illustrated in FIG. 1.

For example, the aerosol generating device 100 may include a heater. The heater may include an electro-resistive heater. For example, the heater may include an electrically conductive track, and the heater may be heated when currents flow through the electrically conductive track. However, the heater is not limited to the example described above and may include all heaters which may be heated to a desired temperature. Here, the desired temperature may be pre-set in the aerosol generating device or may be set at a temperature desired by a user.

As another example, the heater may include an induction heater. Specifically, the heater may include an electrically conductive coil for heating an aerosol generating article in an induction heating method.

The embodiment of FIG. 1 may be applied to other embodiments, and the same reference symbols may denote components that are the same as the above-described components.

Figure 2:
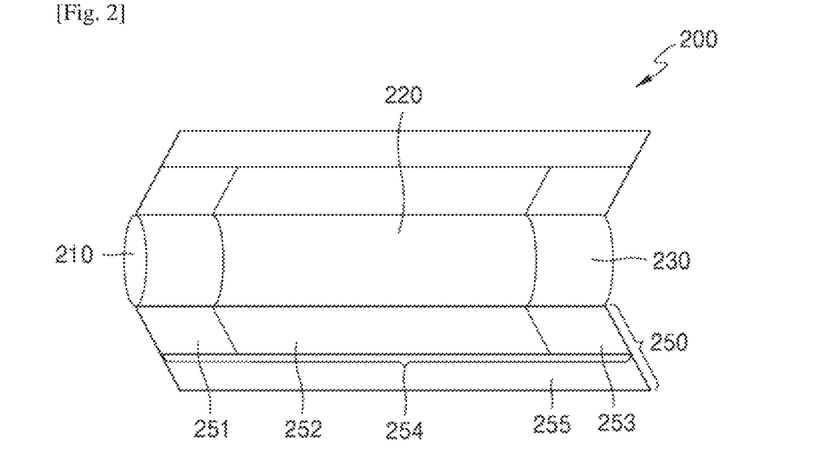
FIG. 2 is a diagram illustrating an example of the aerosol generating article of FIG. 1.

FIG. 2 is a diagram illustrating an example of the aerosol generating article 200 of FIG. 1.

The aerosol generating article 200 includes a tobacco rod 220, a front-end plug 210 located on a side of the tobacco rod 220, and a filter rod 230 disposed on the other side of the tobacco rod 220.

The tobacco rod 220 may include an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol, but it is not limited thereto. Also, the tobacco rod 220 may include other additives, such as flavors, a wetting agent, and/or organic acid. Also, the tobacco rod 220 may include a flavored liquid, such as menthol or a moisturizer, which is injected into the tobacco rod 220.

The tobacco rod 220 may be manufactured in various forms. For example, the tobacco rod 220 may be formed as a sheet or a strand. Also, the tobacco rod 220 may be formed as a pipe tobacco, which is formed of tiny bits cut from a tobacco sheet. Also, the tobacco rod 220 may be surrounded by a heat conductive material. For example, the heat conductive material may be a metal foil such as aluminum foil, but the heat conductive material is not limited thereto.

For example, the heat conductive material surrounding the tobacco rod 220 may uniformly distribute heat to the tobacco rod 220, and thus, the heat conductivity applied to the tobacco rod may be increased and taste of the tobacco may be improved. Also, the heat conductive material surrounding the tobacco rod 220 may function as a susceptor heated by the induction heater. Here, although not illustrated in the drawings, the tobacco rod 220 may further include an additional susceptor, in addition to the heat conductive material surrounding the tobacco rod 220.

The front-end plug 210 disposed on one side of the tobacco rod 220 may include cellulose acetate.

The front-end plug 210 may prevent the tobacco rod 220 from being detached outwardly and prevent the liquefied aerosol from the tobacco rod 220 from flowing into the aerosol generating device 100 of FIG. 1 during smoking.

Also, according to the necessity, the front-end plug 210 may include at least one channel, and a shape of a cross-section of the channel may vary.

The filter rod 230 disposed on the other side of the tobacco rod 220 may cool aerosol flowing from the tobacco rod 220. The filter rod 230 may also filter some components included in an aerosol generated from the tobacco rod 220.

The filter rod 230 may include, for example, cellulous acetate. In this case, the filter rod 230 may be a tube type structure that includes a cavity therein. Although not shown, the filter rod 230 may include at least one capsule. The capsule may generate a flavor and/or an aerosol. For example, the capsule may have a configuration in which a liquid containing a flavoring material is wrapped with a film. The capsule may have a spherical or cylindrical shape, but is not limited thereto.

The aerosol generating article 200 may be wrapped in at least one wrapper 250. The wrapper 250 may include an internal wrapper 254 and an external wrapper 255. In the external wrapper 255 may include at least one hole through which external air flows in or internal air flows out.

The internal wrapper 254 may be wrapped around respective components of the aerosol generating article 200. For example, the front-end plug 210 may be wrapped in a first internal wrapper 251, the tobacco rod 220 may be wrapped in a second internal wrapper 252, and the filter rod 230 may be wrapped in a third internal wrapper 253. The external wrapper 255 may be wrapped around the tobacco rod 220, the front-end plug 210, and the filter rod 230 all at once.

Figure 3:
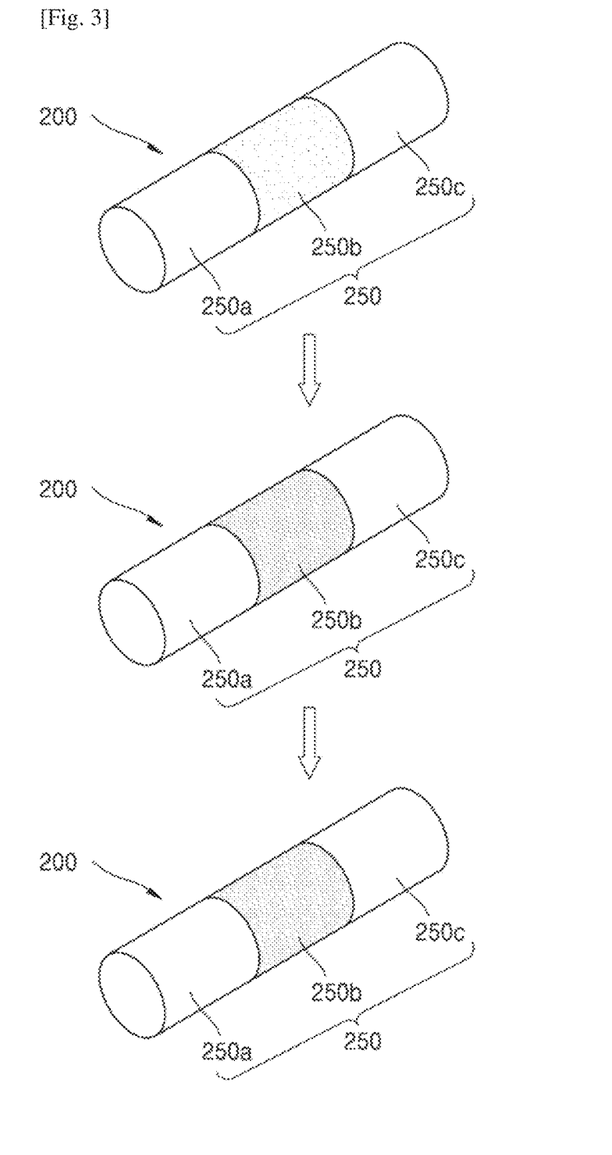
FIG. 3 is a schematic diagram illustrating discoloration of a wrapper when an aerosol generating article is heated.

FIG. 3 is a schematic diagram illustrating discoloration of the wrapper 250 when the aerosol generating article 200 is heated.

The wrapper 250 wrapping the aerosol generating article 200 may include a first area 250a located at a periphery of the front-end plug 210, a second area 250b located at a periphery of the tobacco rod 220, and a third area 250c located at a periphery of the filter rod 230.

Comparing the wrapper 250 of FIG. 3 to that of FIG. 2, the first internal wrapper 251 that wraps the front-end plug 210 and a portion of the external wrapper 255 that wraps the front-end plug 210 may be included in the first area 250a of the wrapper 250. In the second area 250b of the wrapper 250, the second internal wrapper 252 that wraps the tobacco rod 220 and a portion of the external wrapper 255 that wraps the tobacco rod 220 may be included. In the third area 250c of the wrapper 250, the third internal wrapper 253 that wraps the filter rod 230 and a portion of the external wrapper 255 that wraps the filter rod 230 may be included.

The wrapper 250 may be discolored at a temperature of about 50° C. to about 300° C. FIG. 3 illustrates that the second area 250b of the wrapper 250 is discolored, but one or more embodiment are not limited thereto. The wrapper 250 may be discolored in at least one of the first area 250a, the second area 250b, and the third area 250c.

The wrapper 250 may be discolored as the aerosol generating article 200 is heated, and a discoloration degree may increase as a time, at which the aerosol generating article 200 is heated, has passed. Arrows in FIG. 3 may indicate the passage of time with respect to the heating of the aerosol generating article 200, and the discoloration degree of the wrapper 250 may increase along the arrows. However, the discoloration of the wrapper 250 of FIG. 3 is merely an example, and a discoloration degree, a discoloration location, and the time of the wrapper 250 may change according to the necessity.

The wrapper 250 may include a thermochromic material in at least one of the first area, the second area, and the third area. In this case, the thermochromic material may increase a discoloration sensitivity of the wrapper 250.

For example, when the thermochromic material is included in the second area, a discoloration sensitivity of the second area where the thermochromic material is included may be greater than a discoloration sensitivity of a second area where the thermochromic material is not included. An increase in the discoloration sensitivity may indicate that a spectrum of color between the wrapper 250 before discoloration and the wrapper 250 after discoloration increases, and thus, the user may easily identify the discoloration of the wrapper 250.

The thermochromic material included in the wrapper 250 may be discolored in a range between about 50° C. and about 300° C. Preferably, the thermochromic material may be discolored in a range between about 100° C. and about 250° C., but the temperature range is not limited thereto.

Also, the thermochromic material may be discolored after, for example, one minute or 10 minutes from a point in time when the aerosol generating article 200 is heated. Preferably, the thermochromic material may be discolored after three to six minutes from the point in time when the aerosol generating article 200 is heated, but a time taken when the thermochromic material is discolored is not limited to the above-described temporal range.

The thermochromic material may be discolored into black, blue, sky blue, magenta, cyan, red, orange, yellow, purple, green, or the like, but is not limited thereto.

Also, the thermochromic material may be included in 10 wt % in the wrapper 250. Preferably, the thermochromic material may be included in a range from about 0.1 wt % to about 5 wt % in the wrapper 250, but the weight of the thermochromic material is not limited to the above-described range.

The thermochromic material may be coated or printed on the wrapper 250. Alternatively, the thermochromic material may be dyed on the wrapper 250. The thermochromic material may include at least one of a cellulose-based material, a starch-based material, a polyamide-based material, organic acid, and a pigment.

For example, the organic acid included in the thermochromic material may include at least any one of boric acid, oxalic acid, maleic acid, tartaric acid, citric acid, gallic acid, succinic acid, benzoic acid, stearic acid, salicylic acid, tannic acid, uric acid, trimellitic acid, pyromellitic acid, phthalic acid, terephthalic acid, anthranilic acid, 1-hydroxy-2-naphthoic acid, m-hydroxybenzoic acid, 2-hydroxy-p-toluic acid, methylenebis(salicylic acid), p-oxybenzoic acid, β-naphthoic acid, or a combination thereof.

Also, the pigment included in the thermochromic material may include at least any one of bis-dimethylammonium tetrachloronickelate, bis-diethylammonium tetrachlorocuprate, vanadium dioxide, nickel sulfate, or a combination thereof.

Figure 4:
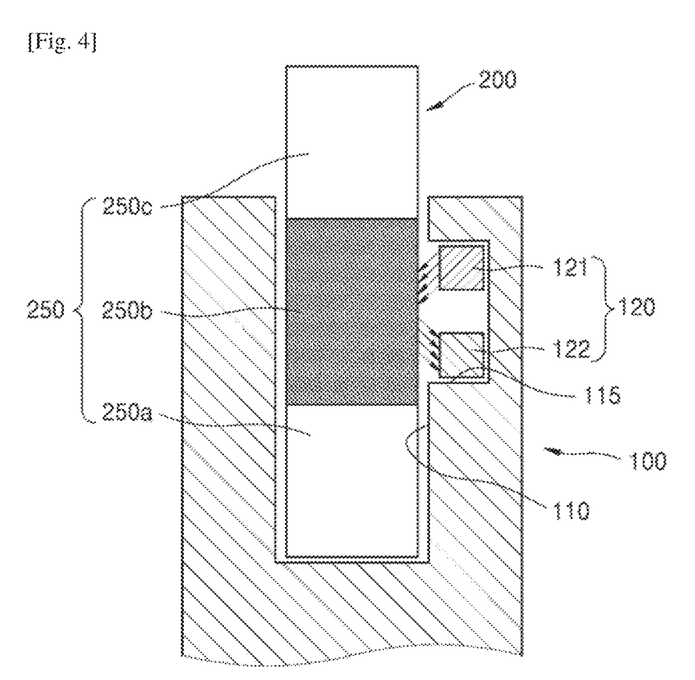
FIG. 4 is a cross-sectional view of an aerosol generating system according to another embodiment.

FIG. 4 is a cross-sectional view of the aerosol generating system 1000 according to another embodiment.

The sensor 120 of the aerosol generating system 1000 according to another embodiment may include a light source 121, which emits light to the aerosol generating article 200, and a vision sensor 122 which receives light reflected from the aerosol generating article 200 after the light is emitted from the light source 121, to detect discoloration.

When the aerosol generating article 200 is reused, the aerosol generating article 200, which is discolored as shown in FIG. 4, may be inserted into the accommodation unit 110.

The sensor 120 may be disposed at a location corresponding to a portion of the wrapper 250 in which the thermochromic material is included. For example, when the thermochromic material is included in the second area of the wrapper 250, the sensor 120 may be disposed at the location corresponding to the second area. In this case, the portion of the wrapper 250, in which the thermochromic material is included, and an area of the sensor 120 are not limited to the drawings and the above description, and may change according to the necessity.

The light source 121 of the sensor 120 may emit the light to the aerosol generating article 200. The light source 121 of the sensor 120 may emit the light to the portion of the wrapper 250 that is discolored. The light that is emitted from the sensor 120 may be reflected from the aerosol generating article 200 and may be received by the vision sensor 122. In this case, the light emitted from the sensor 120 may be reflected from the discolored portion of the wrapper 250 of the aerosol generating article 200.

The vision sensor 122 may receive the light reflected from the aerosol generating article 200 and may detect the discoloration of the wrapper 250. The vision sensor 122 may determine whether the wrapper 250 is discolored according to at least one of standards such as a light intensity, an illumination intensity, and a brightness of the received light.

The vision sensor 122 may perform a dichroic process to distinguish, for example, the wrapper 250 before the discoloration and the wrapper 250 after the discoloration from each other. The dichroic process may be a process of classifying the received light into two categories to distinguish the wrapper 250 before and after the discoloration. The dichroic process may be performed by classifying at least one of the light intensity, the illumination intensity, and the brightness of the received light into two categories. In this case, the dichroic process may be set in advance to distinguish a white color, which is a color of the wrapper 250 before the discoloration, from other colors, and the dichroic process may be performed by the vision sensor 122.

Also, the vision sensor 122 may be an image sensor. When the vision sensor 122 is an image sensor, the vision sensor 122 may generate an image by storing the light reflected from the aerosol generating article 200 and may detect the discoloration by analyzing the generated image.

Figure 5:
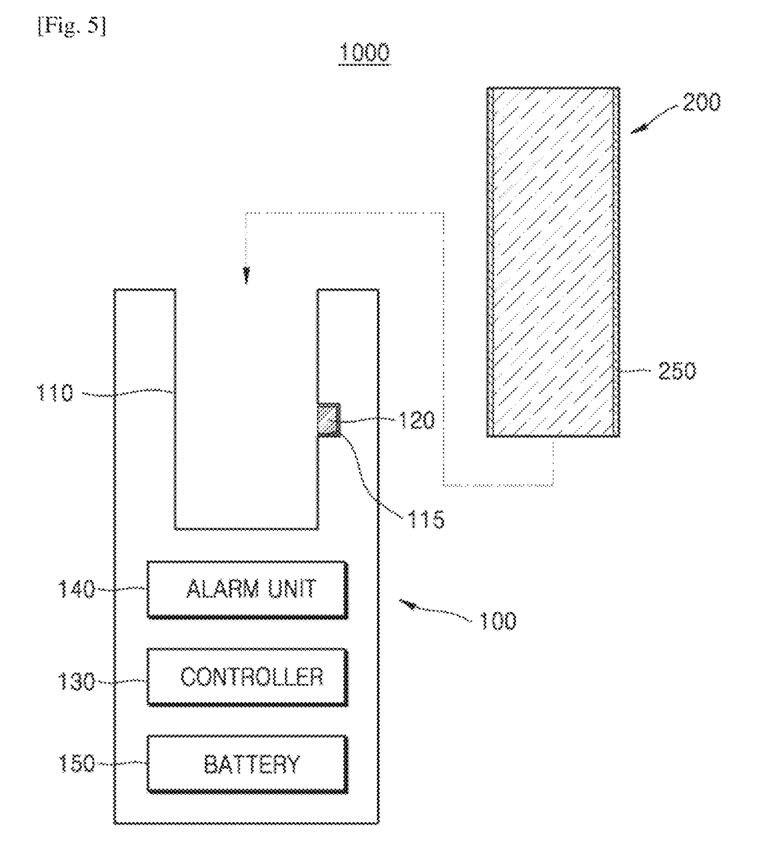
FIG. 5 is a cross-sectional view of an aerosol generating system according to another embodiment.

FIG. 5 is a diagram of the aerosol generating system 1000 according to another embodiment.

The aerosol generating device 100 may further include a battery 150 and a controller 130.

The battery 150 may supply power to operate the aerosol generating device 100. For example, the battery 150 may supply power to operate a heater (not shown) to transmit heat to the aerosol generating article 200. Also, the battery 150 may supply power to drive a sensor, a motor, and the like which may be included in the aerosol generating device 100.

The controller 130 may control overall operations of the aerosol generating device 100. Specifically, the controller 130 may drive the aerosol generating device 100 by controlling the battery 150. The controller 130 may control operations of other components included in the aerosol generating device 100. Also, the controller 130 may identify a state of each component of the aerosol generating device 100 and may determine whether the aerosol generating device 100 is operable.

The controller 130 may include at least one processor. A processor can be implemented as an array of a plurality of logic gates or can be implemented as a combination of a general-purpose microprocessor and a memory in which a program executable in the microprocessor is stored. It will be understood by one of ordinary skill in the art that the processor can be implemented in other forms of hardware.

The controller 130 may be electrically connected to the sensor 120 and may control the operation of the aerosol generating device 100. For example, when the sensor 120 detects the discoloration of the wrapper 250, the sensor 120 may transmit a discoloration detection signal to the controller 130.

The discoloration detection signal may be generated when the aerosol generating article 200 is re-inserted into the accommodation unit 110. That is, after the aerosol generating article 200 is initially used, the wrapper 250 of the aerosol generating article 200 may be discolored. When the aerosol generating article 200 including the discolored wrapper 250 is inserted into the accommodation unit 110, the discoloration of the wrapper 250 may be detected by the sensor 120. The sensor 120 may generate the discoloration detection signal based on detecting the discoloration of the wrapper 250 and may transmit the generated discoloration detection signal to the controller 130. When the controller 130 receives the discoloration detection signal from the sensor 120, the controller 130 may detect the reuse of the aerosol generating article 200 and may stop the operation of the aerosol generating device 100.

As another example, when the sensor 120 does not detect the discoloration of the wrapper 250 of the aerosol generating article 200, the sensor 120 may transmit a discoloration non-detection signal to the controller 130. When the discoloration non-detection signal is transmitted from the sensor 120, the controller 130 may identify the aerosol generating article 200 as new and may allow the aerosol generating device 100 to normally operate.

The transmission of the discoloration detection signal to the controller 130 may be one of conditions under which the aerosol generating device 100 normally operates. That is, according to the transmission of the discoloration detection signal from the sensor 120 to the controller 130, the normal operation of the aerosol generating device 100 may be determined. For example, when the discoloration detection signal is transmitted from the sensor 120 to the controller 130, the controller 130 may control a power output of the battery 150 to block the normal operation of the aerosol generating device 100.

As another example, when the discoloration detection signal is transmitted from the sensor 120 to the controller 130, the controller 130 may generate an alarm signal that notifies the user of the reuse of the aerosol generating article 200.

The aerosol generating device 100 may further include an alarm unit 140. The alarm unit 140 may be at least one of a vibrator, a speaker, and a display. The alarm unit 140 may be mounted on the aerosol generating device 100 and may notify the user of a state of the aerosol generating device 100. The alarm unit 140 may transmit, to the user, at least one of a vibration, a sound, and a light output in response to the alarm signal from the controller 130.

For example, the display may be mounted on the aerosol generating device 100 as the alarm unit 140. In this case, when the discoloration detection signal is transmitted to the controller 130 according to the re-insertion of the aerosol generating article 200 including the discolored wrapper 250, the controller 130 may generate the alarm signal that notifies the user of the reuse of the aerosol generating article 200.

The alarm signal generated by the controller 130 may be transmitted to the display that is the alarm unit 140, and the display may transmit an optical signal that notifies the user of the reuse of the aerosol generating article 200. In this case, the optical signal may be a certain image or text by which the user may identify the reuse of the aerosol generating article 200.

The aerosol generating system 1000 according to embodiments may detect the discoloration of the wrapper 250 of the inserted aerosol generating article 200 to detect the re-insertion and reuse of the aerosol generating article 200.

When the reuse of the aerosol generating article 200 is detected, the operation of the aerosol generating device 100 may be blocked. Alternatively, the reuse of the aerosol generating article 200 may be notified to the user by the alarm unit 140 installed in the aerosol generating device 100.

By blocking the reuse of the aerosol generating article 200, a decrease in the user satisfaction due to an aerosol flavor change, may be prevented.

The aerosol generating device 100 according to another embodiment may include the accommodation unit 110 receiving the aerosol generating article 200 including the wrapper 250, the sensor 120 detecting the discoloration of the wrapper 250, and the controller 130 electrically connected to the sensor 120, and when detecting the discoloration of the wrapper 250, the sensor 120 may transmit the discoloration detection signal to the controller 130.

The sensor 120 may include the light source 121, which emits light to the aerosol generating article 200, and the vision sensor 122, which receives light reflected from the aerosol generating article 200 after the light is emitted from the light source 121, to detect discoloration.

Structures and effects of the aerosol generating device 100 according to another embodiment are the same as described above, and thus, redundant descriptions thereof will be omitted.

At least one of the components, elements, modules or units (collectively "components" in this paragraph) represented by a block in the drawings, such as the controller 130 and the alarm unit 140 in FIG. 5, may be embodied as various numbers of hardware, software and/or firmware structures that execute respective functions described above, according to an exemplary embodiment. For example, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Further, although a bus is not illustrated in the above block diagrams, communication between the components may be performed through the bus. Functional aspects of the above exemplary embodiments may be implemented in algorithms that execute on one or more processors. Furthermore, the components represented by a block or processing steps may employ any number of related art techniques for electronics configuration, signal processing and/or control, data processing and the like.

Those of ordinary skill in the art related to the embodiments of the disclosure may understand that various changes in form and details can be made therein without departing from the scope of the disclosure. The embodiments described above should be considered in a descriptive sense only and should not be construed as limiting the scope of the disclosure. The scope of the present disclosure is defined by the appended claims, and any modifications, substitutions, improvements and equivalents thereof should be construed as being included in the present disclosure.

The invention claimed is:

1. An aerosol generating system comprising:
an aerosol generating article; and
an aerosol generating device configured to receive and heat the aerosol generating article,
wherein the aerosol generating article comprises a wrapper that is heated to be discolored,
wherein the aerosol generating device comprises a sensor that is configured to detect a discoloration of the wrapper, and
wherein the sensor comprises:
a light source configured to emit light to the aerosol generating article; and
a vision sensor configured to receive light reflected from the aerosol generating article to detect the discoloration, the vision sensor performs a dichroic process of classifying the received light into two categories to distinguish the wrapper before the discoloration and the wrapper after the discoloration from each other.

2. The aerosol generating system of claim 1, wherein
the aerosol generating article is inserted into an accommodation unit of the aerosol generating device,
the sensor is mounted on an inner surface of the accommodation unit, and
based on the aerosol generating article being inserted into the accommodation unit, the wrapper is positioned to be adjacent to the sensor.

3. The aerosol generating system of claim 2, wherein the sensor is mounted in a cavity formed in the inner surface of the accommodation unit.

4. The aerosol generating system of claim 1, wherein the aerosol generating article comprises:
a tobacco rod;
a front-end plug arranged on one side of the tobacco rod; and
a filter rod arranged on the other side of the tobacco rod,
wherein the wrapper is wrapped around the tobacco rod, the front-end plug, and the filter rod, and
wherein the wrapper is discolored at a temperature between about 50° C. and about 300° C.

5. The aerosol generating system of claim 4, wherein
the wrapper comprises a first area located at a first periphery of the front-end plug, a second area located at a second periphery of the tobacco rod, and a third area at a third periphery of the filter rod, and
the wrapper is discolored in at least one of the first area, the second area, and the third area.

6. The aerosol generating system of claim 5, wherein the wrapper comprises a thermochromic material in at least one of the first area, the second area, and the third area.

7. The aerosol generating system of claim 6, wherein the thermochromic material comprises at least any one of a cellulous-based material, a starch-based material, a polyamide-based material, organic acid, and a pigment.

8. The aerosol generating system of claim 1, further comprising a controller electrically connected to the sensor,
wherein the sensor is configured to transmit a discoloration detection signal to the controller.

9. The aerosol generating system of claim 8, wherein, based on the controller receiving the discoloration detection signal, the controller is configured to block operation of the aerosol generating device.

10. The aerosol generating system of claim 8, wherein, based on the controller receiving the discoloration detection signal, the controller is configured to generate an alarm signal that notifies a user of a reuse the aerosol generating article.

11. The aerosol generating system of claim 10, further comprising an alarm unit comprising at least one of a vibrator, a speaker, and a display,
wherein the alarm unit is configured to transmit, to the user, at least one of a vibration, a sound, and a light output in response to the alarm signal from the controller.

12. An aerosol generating device comprising:
an accommodation unit configured to receive an aerosol generating article comprising a wrapper;
a sensor configured to detect a discoloration of the wrapper; and
a controller electrically connected to the sensor,
wherein, based on the discoloration of the wrapper being detected, the sensor is configured to transmit a discoloration detection signal to the controller, and
wherein the sensor comprises:
a light source configured to emit light to the aerosol generating article; and
a vision sensor configured receive light reflected from the aerosol generating article to detect the discoloration, the vision sensor performs a dichroic process of classifying the received light into two categories to distinguish the wrapper before the discoloration and the wrapper after the discoloration from each other.

* * * * *